(12) United States Patent
Gershony et al.

(10) Patent No.: US 9,364,254 B2
(45) Date of Patent: Jun. 14, 2016

(54) METHOD AND SYSTEM FOR TREATING VALVE STENOSIS

(71) Applicant: AngioScore, Inc., Colorado Springs, CO (US)

(72) Inventors: Gary Gershony, Piedmont, CA (US); David Doty, Forestville, CA (US)

(73) Assignee: AngioScore, Inc., Colorado Springs, CO (US)

( * ) Notice: Subject to any disclaimer, the term of this patent is extended or adjusted under 35 U.S.C. 154(b) by 0 days.

(21) Appl. No.: 13/894,613

(22) Filed: May 15, 2013

(65) Prior Publication Data

US 2013/0253554 A1 Sep. 26, 2013

Related U.S. Application Data

(62) Division of application No. 13/236,449, filed on Sep. 19, 2011, now Pat. No. 8,632,559.

(60) Provisional application No. 61/384,800, filed on Sep. 21, 2010.

(51) Int. Cl.
*A61B 17/3207* (2006.01)
*A61B 17/22* (2006.01)

(52) U.S. Cl.
CPC ..... *A61B 17/3207* (2013.01); *A61B 17/320725* (2013.01); *A61B 2017/22061* (2013.01); *A61B 2017/22098* (2013.01)

(58) Field of Classification Search
CPC .................. A61B 17/3207; A61B 17/320725; A61B 2017/22098

USPC ......... 606/159, 194, 195, 198–200; 623/1.14, 623/1.36, 2.11

See application file for complete search history.

(56) References Cited

U.S. PATENT DOCUMENTS

| | | | |
|---|---|---|---|
| 2,701,559 A | 2/1955 | Cooper | |
| 2,854,983 A | 10/1958 | Baskin | |
| 3,045,677 A | 7/1962 | Wallace | |
| 3,467,101 A | 9/1969 | Fogarty et al. | |
| 3,825,013 A | 7/1974 | Craven | |

(Continued)

FOREIGN PATENT DOCUMENTS

| | | |
|---|---|---|
| EP | 0565796 B1 | 5/1997 |
| EP | 0623315 B1 | 6/1999 |

(Continued)

OTHER PUBLICATIONS

International search report and written opinion dated Jan. 11, 2012 for PCT/2011/052392.

(Continued)

*Primary Examiner* — Thomas McEvoy
(74) *Attorney, Agent, or Firm* — Faegre Baker Daniels LLP

(57) ABSTRACT

A valvuloplasty catheter comprises a balloon or other expansible shell which carries a plurality of scoring elements, typically formed in an elastic, self-closing metal cage. The expansible shell and scoring elements are positioned inside an aortic or other cardiac valve, and the shell expanded to engage the scoring elements against stenotic material which covers the valve leaflets and valve annulus. The scoring elements uniformly distributed force to break up the stenotic material, and the cage further contributes to rapid balloon deflation allowing shortening of the treatment time.

6 Claims, 5 Drawing Sheets

(56) References Cited

U.S. PATENT DOCUMENTS

| | | |
|---|---|---|
| 4,327,736 A | 5/1982 | Inoue |
| 4,456,011 A | 6/1984 | Warnecke |
| 4,483,340 A | 11/1984 | Fogarty et al. |
| 4,604,762 A | 8/1986 | Robinson |
| 4,637,396 A | 1/1987 | Cook |
| 4,649,922 A | 3/1987 | Wiktor |
| 4,723,549 A | 2/1988 | Wholey et al. |
| 4,733,665 A | 3/1988 | Palmaz |
| 4,796,629 A | 1/1989 | Grayzel |
| 4,838,853 A | 6/1989 | Parisi |
| 4,887,613 A | 12/1989 | Farr et al. |
| 4,895,166 A | 1/1990 | Farr et al. |
| 4,921,484 A | 5/1990 | Hillstead |
| 4,942,788 A | 7/1990 | Farr et al. |
| 4,950,277 A | 8/1990 | Farr |
| 4,956,830 A | 9/1990 | Mock et al. |
| 4,969,458 A | 11/1990 | Wiktor |
| 4,976,711 A | 12/1990 | Parins et al. |
| 4,986,807 A | 1/1991 | Farr |
| 4,986,830 A | 1/1991 | Owens et al. |
| 4,998,539 A | 3/1991 | Delsanti |
| 5,003,918 A | 4/1991 | Olson et al. |
| 5,019,088 A | 5/1991 | Farr |
| 5,019,089 A | 5/1991 | Farr |
| 5,026,384 A | 6/1991 | Farr et al. |
| 5,062,384 A | 11/1991 | Foley et al. |
| 5,062,648 A | 11/1991 | Gomringer |
| 5,071,407 A | 12/1991 | Termin et al. |
| 5,098,440 A | 3/1992 | Hillstead |
| 5,100,386 A | 3/1992 | Inoue |
| 5,100,423 A | 3/1992 | Fearnot |
| 5,101,682 A | 4/1992 | Radisch et al. |
| 5,102,402 A | 4/1992 | Dror et al. |
| 5,102,417 A | 4/1992 | Palmaz |
| 5,108,416 A | 4/1992 | Ryan et al. |
| 5,112,345 A | 5/1992 | Farr |
| 5,116,318 A | 5/1992 | Hillstead |
| 5,120,322 A | 6/1992 | Davis et al. |
| 5,133,732 A | 7/1992 | Wiktor |
| 5,176,693 A | 1/1993 | Pannek et al. |
| 5,181,911 A | 1/1993 | Shturman |
| 5,190,058 A | 3/1993 | Jones et al. |
| 5,192,291 A | 3/1993 | Pannek et al. |
| 5,196,024 A | 3/1993 | Barath |
| 5,209,727 A | 5/1993 | Radisch et al. |
| 5,222,971 A | 6/1993 | Willard et al. |
| 5,224,945 A | 7/1993 | Pannek et al. |
| 5,224,949 A | 7/1993 | Gomringer et al. |
| 5,226,887 A | 7/1993 | Farr et al. |
| 5,243,997 A | 9/1993 | Uflacker et al. |
| 5,263,963 A | 11/1993 | Garrison et al. |
| 5,295,493 A | 3/1994 | Radisch et al. |
| 5,295,959 A | 3/1994 | Gurbel et al. |
| 5,304,121 A | 4/1994 | Sahatjian |
| 5,306,250 A | 4/1994 | March et al. |
| 5,308,354 A | 5/1994 | Zacca et al. |
| 5,308,356 A | 5/1994 | Blackshear, Jr. et al. |
| 5,318,576 A | 6/1994 | Plassche, Jr. et al. |
| 5,320,634 A | 6/1994 | Vigil et al. |
| 5,336,178 A | 8/1994 | Kaplan et al. |
| 5,336,234 A | 8/1994 | Vigil et al. |
| 5,344,401 A | 9/1994 | Radisch et al. |
| 5,344,419 A | 9/1994 | Spears |
| 5,350,101 A | 9/1994 | Godlewski |
| 5,423,745 A | 6/1995 | Todd et al. |
| 5,443,078 A | 8/1995 | Uflacker |
| 5,443,446 A | 8/1995 | Shturman |
| 5,443,496 A | 8/1995 | Schwartz et al. |
| 5,449,372 A | 9/1995 | Schmaltz et al. |
| 5,449,373 A | 9/1995 | Pinchasik et al. |
| 5,456,666 A | 10/1995 | Campbell et al. |
| 5,456,667 A | 10/1995 | Ham et al. |
| 5,458,568 A | 10/1995 | Racchini et al. |
| 5,460,607 A | 10/1995 | Miyata et al. |
| 5,470,314 A | 11/1995 | Walinsky |
| 5,501,694 A | 3/1996 | Ressemann et al. |
| 5,524,635 A | 6/1996 | Uflacker et al. |
| 5,527,282 A | 6/1996 | Segal |
| 5,536,178 A | 7/1996 | Novelli |
| 5,545,132 A | 8/1996 | Fagan et al. |
| 5,556,405 A | 9/1996 | Lary |
| 5,556,408 A | 9/1996 | Farhat |
| 5,562,620 A | 10/1996 | Klein et al. |
| 5,569,195 A | 10/1996 | Saab |
| 5,571,086 A | 11/1996 | Kaplan et al. |
| 5,607,442 A | 3/1997 | Fischell et al. |
| 5,609,574 A | 3/1997 | Kaplan et al. |
| 5,616,149 A | 4/1997 | Barath |
| 5,620,457 A | 4/1997 | Pinchasik et al. |
| 5,624,433 A | 4/1997 | Radisch et al. |
| 5,628,746 A | 5/1997 | Clayman |
| 5,628,755 A | 5/1997 | Heller et al. |
| 5,643,210 A | 7/1997 | Iacob |
| 5,649,941 A | 7/1997 | Lary |
| 5,681,281 A | 10/1997 | Vigil et al. |
| 5,690,642 A | 11/1997 | Osborne et al. |
| 5,695,469 A | 12/1997 | Segal |
| 5,697,944 A | 12/1997 | Lary |
| 5,697,971 A | 12/1997 | Fischell et al. |
| 5,702,410 A | 12/1997 | Klunder et al. |
| 5,707,385 A | 1/1998 | Williams |
| 5,713,863 A | 2/1998 | Vigil et al. |
| 5,713,913 A | 2/1998 | Lary et al. |
| 5,718,684 A | 2/1998 | Gupta |
| 5,730,698 A | 3/1998 | Fischell et al. |
| 5,733,303 A | 3/1998 | Israel et al. |
| 5,735,816 A | 4/1998 | Lieber et al. |
| 5,742,019 A | 4/1998 | Radisch et al. |
| 5,755,708 A | 5/1998 | Segal |
| 5,755,781 A | 5/1998 | Jayaraman |
| 5,766,201 A | 6/1998 | Ravenscroft et al. |
| 5,766,238 A | 6/1998 | Lau et al. |
| 5,772,681 A | 6/1998 | Leoni |
| 5,776,141 A | 7/1998 | Klein et al. |
| 5,776,181 A | 7/1998 | Lee et al. |
| 5,792,144 A | 8/1998 | Fischell et al. |
| 5,792,415 A | 8/1998 | Hijlkema |
| 5,797,935 A | 8/1998 | Barath |
| 5,807,355 A | 9/1998 | Ramzipoor et al. |
| 5,810,767 A | 9/1998 | Klein |
| 5,814,061 A | 9/1998 | Osborne et al. |
| 5,827,321 A | 10/1998 | Roubin et al. |
| 5,863,284 A | 1/1999 | Klein |
| 5,868,708 A | 2/1999 | Hart et al. |
| 5,868,719 A | 2/1999 | Tsukernik |
| 5,868,779 A | 2/1999 | Ruiz |
| 5,868,783 A | 2/1999 | Tower |
| 5,869,284 A | 2/1999 | Cao et al. |
| 5,891,090 A | 4/1999 | Thornton |
| 5,902,475 A | 5/1999 | Trozera et al. |
| 5,904,679 A | 5/1999 | Clayman |
| 5,904,698 A | 5/1999 | Thomas et al. |
| 5,906,639 A | 5/1999 | Rudnick et al. |
| 5,916,166 A | 6/1999 | Reiss et al. |
| 5,919,200 A | 7/1999 | Stambaugh et al. |
| 5,954,742 A | 9/1999 | Osypka |
| 5,961,490 A | 10/1999 | Adams |
| 5,967,984 A | 10/1999 | Chu et al. |
| 5,980,486 A | 11/1999 | Enger |
| 5,987,661 A | 11/1999 | Peterson |
| 5,994,667 A | 11/1999 | Merdan et al. |
| 6,013,055 A | 1/2000 | Bampos et al. |
| 6,036,686 A | 3/2000 | Griswold |
| 6,036,689 A | 3/2000 | Tu et al. |
| 6,036,708 A | 3/2000 | Sciver |
| 6,048,356 A | 4/2000 | Ravenscroft et al. |
| 6,053,913 A | 4/2000 | Tu et al. |
| 6,059,811 A | 5/2000 | Pinchasik et al. |
| 6,071,285 A | 6/2000 | Lashinski et al. |
| 6,071,286 A | 6/2000 | Mawad |
| 6,077,298 A | 6/2000 | Tu et al. |
| RE36,764 E | 7/2000 | Zacca et al. |
| 6,102,904 A * | 8/2000 | Vigil et al. ............... 604/500 |
| 6,106,548 A | 8/2000 | Roubin et al. |

(56) References Cited

U.S. PATENT DOCUMENTS

| | | |
|---|---|---|
| 6,117,104 A | 9/2000 | Fitz |
| 6,117,153 A | 9/2000 | Lary et al. |
| 6,123,718 A | 9/2000 | Tu et al. |
| 6,129,706 A | 10/2000 | Janacek |
| 6,129,708 A | 10/2000 | Enger |
| 6,136,011 A | 10/2000 | Stambaugh |
| 6,146,323 A | 11/2000 | Fischell |
| 6,152,944 A | 11/2000 | Holman et al. |
| 6,156,254 A | 12/2000 | Andrews et al. |
| 6,156,265 A | 12/2000 | Sugimoto |
| 6,165,187 A | 12/2000 | Reger |
| 6,190,356 B1 | 2/2001 | Bersin |
| 6,190,403 B1 | 2/2001 | Fischell et al. |
| 6,193,686 B1 | 2/2001 | Estrada et al. |
| 6,203,569 B1 | 3/2001 | Wijay |
| 6,206,910 B1 | 3/2001 | Berry et al. |
| 6,210,392 B1 | 4/2001 | Vigil et al. |
| 6,224,625 B1 | 5/2001 | Jayaraman |
| 6,235,043 B1 | 5/2001 | Reiley et al. |
| 6,241,762 B1 | 6/2001 | Shanley |
| 6,245,040 B1 | 6/2001 | Inderbitzen et al. |
| 6,258,087 B1 | 7/2001 | Edwards et al. |
| 6,258,099 B1 | 7/2001 | Mareiro et al. |
| 6,258,108 B1 | 7/2001 | Lary |
| 6,261,319 B1 | 7/2001 | Kveen et al. |
| 6,261,630 B1 | 7/2001 | Nazarova et al. |
| 6,287,336 B1 | 9/2001 | Globerman et al. |
| 6,289,568 B1 | 9/2001 | Miller et al. |
| 6,296,651 B1 | 10/2001 | Lary et al. |
| 6,306,151 B1 | 10/2001 | Lary |
| 6,306,166 B1 | 10/2001 | Barry et al. |
| 6,309,414 B1 | 10/2001 | Rolando et al. |
| 6,312,459 B1 | 11/2001 | Huang et al. |
| 6,319,229 B1 | 11/2001 | Kim et al. |
| 6,319,242 B1 | 11/2001 | Patterson et al. |
| 6,319,251 B1 | 11/2001 | Tu et al. |
| 6,325,779 B1 | 12/2001 | Zedler |
| 6,325,813 B1 | 12/2001 | Hektner |
| 6,332,880 B1 | 12/2001 | Yang et al. |
| 6,355,013 B1 | 3/2002 | van Muiden |
| 6,355,059 B1 | 3/2002 | Richter et al. |
| 6,361,545 B1 | 3/2002 | Macoviak et al. |
| 6,364,856 B1 | 4/2002 | Ding et al. |
| 6,371,961 B1 | 4/2002 | Osborne et al. |
| 6,394,995 B1 | 5/2002 | Solar et al. |
| 6,416,494 B1 | 7/2002 | Wilkins |
| 6,416,539 B1 | 7/2002 | Hassdenteufel |
| 6,425,882 B1 | 7/2002 | Vigil |
| 6,425,908 B2 | 7/2002 | Ravenscroft et al. |
| 6,440,158 B1 | 8/2002 | Saab |
| 6,447,501 B1 | 9/2002 | Solar et al. |
| 6,450,988 B1 | 9/2002 | Bradshaw |
| 6,450,989 B2 | 9/2002 | Dubrul et al. |
| 6,454,775 B1 | 9/2002 | Demarais et al. |
| 6,471,979 B2 | 10/2002 | New et al. |
| 6,475,233 B2 | 11/2002 | Trozera |
| 6,475,234 B1 | 11/2002 | Richter et al. |
| 6,475,236 B1 | 11/2002 | Roubin et al. |
| 6,478,807 B1 | 11/2002 | Foreman et al. |
| 6,500,186 B2 | 12/2002 | Lafontaine et al. |
| 6,517,765 B1 | 2/2003 | Kelley |
| 6,540,722 B1 | 4/2003 | Boyle et al. |
| 6,551,310 B1 | 4/2003 | Ganz et al. |
| 6,554,795 B2 | 4/2003 | Bagaoisan et al. |
| 6,562,062 B2 | 5/2003 | Jenusaitis et al. |
| 6,565,528 B1 | 5/2003 | Mueller |
| 6,569,180 B1 | 5/2003 | Sirhan et al. |
| 6,575,993 B1 | 6/2003 | Yock |
| 6,592,548 B2 | 7/2003 | Jayaraman |
| 6,602,281 B1 | 8/2003 | Klein |
| 6,605,107 B1 | 8/2003 | Klein |
| 6,607,442 B2 | 8/2003 | Ogata et al. |
| 6,613,072 B2 | 9/2003 | Lau et al. |
| 6,616,678 B2 | 9/2003 | Nishtala et al. |
| 6,626,861 B1 | 9/2003 | Hart et al. |
| 6,632,231 B2 | 10/2003 | Radisch et al. |
| 6,648,912 B2 | 11/2003 | Trout et al. |
| 6,652,548 B2 | 11/2003 | Evans et al. |
| 6,656,351 B2 | 12/2003 | Boyle |
| 6,663,660 B2 | 12/2003 | Dusbabek et al. |
| 6,695,813 B1 | 2/2004 | Boyle et al. |
| 6,743,196 B2 | 6/2004 | Barbut et al. |
| 6,746,463 B1 | 6/2004 | Schwartz |
| 6,783,542 B2 | 8/2004 | Eidenschink |
| 6,840,950 B2 | 1/2005 | Stanford et al. |
| 6,872,206 B2 | 3/2005 | Edwards et al. |
| 6,918,920 B1 | 7/2005 | Wang et al. |
| 6,939,320 B2 | 9/2005 | Lennox |
| 6,942,680 B2 | 9/2005 | Grayzel et al. |
| 6,951,566 B2 | 10/2005 | Lary |
| 7,011,654 B2 | 3/2006 | Dubrul et al. |
| 7,011,670 B2 | 3/2006 | Radisch et al. |
| 7,029,483 B2 | 4/2006 | Schwartz |
| 7,060,051 B2 | 6/2006 | Palasis |
| 7,131,981 B2 | 11/2006 | Appling et al. |
| 7,172,609 B2 | 2/2007 | Radisch et al. |
| 7,186,237 B2 | 3/2007 | Meyer et al. |
| 7,232,432 B2 | 6/2007 | Fulton et al. |
| 7,252,650 B1 | 8/2007 | Andrews et al. |
| 7,303,572 B2 | 12/2007 | Melsheimer et al. |
| 7,354,445 B2 | 4/2008 | Nicholson et al. |
| 7,357,813 B2 | 4/2008 | Burgermeister |
| 7,396,358 B2 | 7/2008 | Appling et al. |
| 7,455,652 B2 | 11/2008 | Laird |
| 7,465,311 B2 | 12/2008 | Wang et al. |
| 7,494,497 B2 | 2/2009 | Weber |
| 7,517,352 B2 | 4/2009 | Evans et al. |
| 7,524,319 B2 | 4/2009 | Dubrul |
| 7,566,319 B2 | 7/2009 | McAuley et al. |
| 7,686,824 B2 | 3/2010 | Konstantino et al. |
| 7,691,119 B2 | 4/2010 | Farnan |
| 7,708,748 B2 | 5/2010 | Weisenburgh, II et al. |
| 7,708,753 B2 | 5/2010 | Hardert |
| 7,736,375 B2 | 6/2010 | Crow |
| 7,763,043 B2 | 7/2010 | Goodin et al. |
| 7,780,715 B2 | 8/2010 | Shaked et al. |
| 7,780,798 B2 | 8/2010 | Stinson et al. |
| 7,931,663 B2 | 4/2011 | Farnan et al. |
| 7,955,350 B2 | 6/2011 | Konstantino et al. |
| 7,963,942 B2 | 6/2011 | Chen |
| 7,976,557 B2 | 7/2011 | Kunis |
| 7,998,184 B2 | 8/2011 | Eidenschink |
| 8,043,259 B2 | 10/2011 | Radisch et al. |
| 8,052,703 B2 | 11/2011 | St. Martin et al. |
| 8,066,726 B2 | 11/2011 | Kelley |
| 8,080,026 B2 | 12/2011 | Konstantino et al. |
| 8,123,770 B2 | 2/2012 | Olsen et al. |
| 8,192,675 B2 | 6/2012 | Burton et al. |
| 8,221,444 B2 | 7/2012 | Wang et al. |
| 8,323,307 B2 | 12/2012 | Hardert |
| 8,348,987 B2 | 1/2013 | Eaton |
| 8,382,820 B2 | 2/2013 | Addonizio et al. |
| 8,454,637 B2 | 6/2013 | Aggerholm et al. |
| 8,574,248 B2 | 11/2013 | Kassab |
| 8,685,050 B2 | 4/2014 | Schur et al. |
| 8,685,990 B2 | 4/2014 | Coats et al. |
| 2001/0001113 A1 | 5/2001 | Lim et al. |
| 2001/0001823 A1 | 5/2001 | Ryan |
| 2001/0007082 A1 | 7/2001 | Dusbabek et al. |
| 2001/0012950 A1 | 8/2001 | Nishtala et al. |
| 2001/0016753 A1 | 8/2001 | Caprio et al. |
| 2002/0010487 A1 | 1/2002 | Evans et al. |
| 2002/0010489 A1 | 1/2002 | Grayzel et al. |
| 2002/0029015 A1 | 3/2002 | Camenzind et al. |
| 2002/0038144 A1 | 3/2002 | Trout et al. |
| 2002/0045930 A1 | 4/2002 | Burg et al. |
| 2002/0065548 A1 | 5/2002 | Birdsall et al. |
| 2002/0077606 A1 | 6/2002 | Trotta |
| 2002/0111633 A1 | 8/2002 | Stoltze et al. |
| 2002/0165599 A1 | 11/2002 | Nasralla |
| 2002/0193873 A1 | 12/2002 | Brucker et al. |
| 2003/0018376 A1 | 1/2003 | Solar et al. |
| 2003/0023200 A1 | 1/2003 | Barbut et al. |
| 2003/0028235 A1 | 2/2003 | McIntosh et al. |

(56) References Cited

U.S. PATENT DOCUMENTS

| | | |
|---|---|---|
| 2003/0032973 A1 | 2/2003 | Jenusaitis et al. |
| 2003/0065381 A1 | 4/2003 | Solar et al. |
| 2003/0074046 A1 | 4/2003 | Richter |
| 2003/0078606 A1 | 4/2003 | Lafontaine et al. |
| 2003/0097169 A1 | 5/2003 | Brucker et al. |
| 2003/0105509 A1 | 6/2003 | Jang et al. |
| 2003/0114915 A1 | 6/2003 | Mareiro et al. |
| 2003/0144683 A1 | 7/2003 | Sirhan et al. |
| 2003/0149468 A1 | 8/2003 | Wallsten |
| 2003/0152870 A1 | 8/2003 | Huang |
| 2003/0153870 A1 | 8/2003 | Meyer et al. |
| 2003/0171799 A1 | 9/2003 | Lee et al. |
| 2003/0187494 A1 | 10/2003 | Loaldi |
| 2003/0195609 A1 | 10/2003 | Berenstein et al. |
| 2003/0199970 A1 | 10/2003 | Shanley |
| 2003/0199988 A1 | 10/2003 | Devonec et al. |
| 2003/0208244 A1 | 11/2003 | Stein et al. |
| 2003/0208255 A1 | 11/2003 | O'Shaughnessy et al. |
| 2004/0034384 A1 | 2/2004 | Fukaya |
| 2004/0111108 A1 | 6/2004 | Farnan |
| 2004/0127475 A1 | 7/2004 | New et al. |
| 2004/0133223 A1 | 7/2004 | Weber |
| 2004/0143287 A1 | 7/2004 | Konstantino et al. |
| 2004/0210299 A1 | 10/2004 | Rogers et al. |
| 2004/0230293 A1 | 11/2004 | Yip et al. |
| 2004/0243158 A1 | 12/2004 | Konstantino et al. |
| 2005/0010278 A1 | 1/2005 | Vardi et al. |
| 2005/0021070 A1 | 1/2005 | Feld et al. |
| 2005/0021071 A1 | 1/2005 | Konstantino et al. |
| 2005/0083768 A1 | 4/2005 | Hara |
| 2005/0131512 A1 | 6/2005 | Vonderwalde |
| 2005/0137690 A1 | 6/2005 | Salahieh et al. |
| 2005/0271844 A1 | 12/2005 | Mapes et al. |
| 2006/0015133 A1 | 1/2006 | Grayzel et al. |
| 2006/0074484 A1 | 4/2006 | Huber |
| 2006/0085025 A1 | 4/2006 | Farnan et al. |
| 2006/0112536 A1 | 6/2006 | Herweck et al. |
| 2006/0129093 A1 | 6/2006 | Jackson |
| 2006/0149308 A1 | 7/2006 | Melsheimer et al. |
| 2006/0173487 A1 | 8/2006 | Uflacker et al. |
| 2006/0184191 A1 | 8/2006 | O'Brien |
| 2006/0247674 A1 | 11/2006 | Roman |
| 2006/0259005 A1 | 11/2006 | Konstantino et al. |
| 2006/0259062 A1 | 11/2006 | Konstantino |
| 2006/0270193 A1 | 11/2006 | Hidaka et al. |
| 2007/0112422 A1 | 5/2007 | Dehdashtian |
| 2007/0185513 A1 | 8/2007 | Woolfson et al. |
| 2007/0198047 A1 | 8/2007 | Schon et al. |
| 2007/0213808 A1 | 9/2007 | Roubin et al. |
| 2008/0300610 A1 | 12/2008 | Chambers |
| 2009/0105686 A1 | 4/2009 | Snow et al. |
| 2009/0105687 A1 | 4/2009 | Deckman et al. |
| 2009/0264859 A1 | 10/2009 | Mas |
| 2009/0281490 A1 | 11/2009 | McAuley et al. |
| 2009/0306582 A1 | 12/2009 | Granada et al. |
| 2010/0042121 A1 | 2/2010 | Schneider et al. |
| 2010/0121372 A1 | 5/2010 | Farnan |
| 2010/0179647 A1* | 7/2010 | Carpenter et al. ........... 623/2.11 |
| 2010/0286720 A1 | 11/2010 | Shaked et al. |
| 2010/0286721 A1 | 11/2010 | Goodin et al. |
| 2011/0082483 A1 | 4/2011 | Diamant et al. |
| 2011/0125247 A1 | 5/2011 | Farnan et al. |
| 2011/0152905 A1 | 6/2011 | Eaton |
| 2011/0160756 A1 | 6/2011 | Aggerholm et al. |
| 2011/0264039 A1* | 10/2011 | Thielen et al. ........... 604/103.01 |
| 2011/0270177 A1 | 11/2011 | Chambers et al. |
| 2012/0059401 A1 | 3/2012 | Konstantino et al. |
| 2012/0215251 A1 | 8/2012 | Burton et al. |
| 2012/0277626 A1 | 11/2012 | Burbank et al. |
| 2013/0041391 A1 | 2/2013 | Spencer et al. |
| 2013/0041399 A1 | 2/2013 | Hardert |
| 2013/0060127 A1 | 3/2013 | Burton et al. |
| 2013/0066346 A1 | 3/2013 | Pigott |
| 2013/0096604 A1 | 4/2013 | Hanson et al. |
| 2013/0150874 A1 | 6/2013 | Kassab |
| 2013/0211381 A1 | 8/2013 | Feld |
| 2013/0218181 A1 | 8/2013 | Feld et al. |
| 2013/0253554 A1 | 9/2013 | Gershony et al. |
| 2013/0345730 A1 | 12/2013 | Gershony et al. |
| 2014/0058358 A1 | 2/2014 | Kassab |
| 2014/0066960 A1 | 3/2014 | Feld et al. |
| 2015/0100079 A1 | 4/2015 | Moffarah et al. |

FOREIGN PATENT DOCUMENTS

| | | |
|---|---|---|
| EP | 1169970 A1 | 1/2002 |
| EP | 1179323 A2 | 2/2002 |
| EP | 0832608 B1 | 3/2003 |
| EP | 1042997 B1 | 3/2005 |
| EP | 1581298 B1 | 8/2006 |
| EP | 1414373 B1 | 5/2008 |
| EP | 1337198 B1 | 6/2009 |
| EP | 1748816 B1 | 7/2010 |
| EP | 2063924 B1 | 10/2010 |
| EP | 2283890 A1 | 2/2011 |
| EP | 1962696 B1 | 3/2012 |
| EP | 1737530 B1 | 3/2013 |
| EP | 2564890 A1 | 3/2013 |
| JP | H07503623 A | 4/1995 |
| JP | 2002126086 A | 5/2002 |
| JP | 2002126086 A1 | 5/2002 |
| JP | 2004504111 A | 2/2004 |
| JP | 2004148013 A1 | 5/2004 |
| JP | 2007502694 A | 2/2007 |
| JP | 2011528963 A | 12/2011 |
| JP | 2011529350 A | 12/2011 |
| WO | WO9102494 A1 | 3/1991 |
| WO | 92/17118 A1 | 10/1992 |
| WO | 9217118 A1 | 10/1992 |
| WO | WO9301753 A2 | 2/1993 |
| WO | WO9410919 A1 | 5/1994 |
| WO | WO94023787 A1 | 10/1994 |
| WO | WO9424946 A1 | 11/1994 |
| WO | WO9503083 A1 | 2/1995 |
| WO | WO9805377 A1 | 2/1998 |
| WO | WO9845506 A1 | 10/1998 |
| WO | 9917680 A1 | 4/1999 |
| WO | 9955253 A1 | 11/1999 |
| WO | 9962430 A1 | 12/1999 |
| WO | 02083011 A1 | 10/2002 |
| WO | WO02083011 A1 | 10/2002 |
| WO | WO03026536 A1 | 4/2003 |
| WO | WO03039628 A2 | 5/2003 |
| WO | WO03041760 A2 | 5/2003 |
| WO | WO2004028610 A2 | 4/2004 |
| WO | WO2004060460 A2 | 7/2004 |
| WO | WO2004066852 A2 | 8/2004 |
| WO | WO2005025458 A1 | 3/2005 |
| WO | 2009150099 A1 | 12/2009 |
| WO | 2015054277 A1 | 4/2015 |

OTHER PUBLICATIONS

Extended European Search Report dated Apr. 7, 2014, for related EP application No. 11827369.7.

European search report and search opinion dated May 4, 2010 for EP 06770116.9.

European search report and search opinion dated Dec. 28, 2009 for EP 05792875.6.

Extended European Search Report issued in EP Application No. 11827369.7, mailed Apr. 7, 2014. 6 pages.

File History for U.S. Appl. No. 13/044,425, filed Mar. 9, 2011.

First Examination Report dated Feb. 5, 2014 from corresponding EP Application No. 05733012.8.

International search report and written opinion dated Feb. 27, 2007 for PCT/US2006/017872.

International search report and written opinion dated May 23, 2006 for PCT /2005/009571.

International search report and written opinion dated Jul. 26, 2007 for PCT/2005/028809.

International search report and written opinion dated Nov. 4, 2004 for PCT/2004/000177.

(56) References Cited

OTHER PUBLICATIONS

International Search Report and Written Opinion issued in PCT/US2011/052392 mailed Jan. 11, 2012, 7 pages.
International Search Report issued in PCT/US2002/035547 dated May 20, 2003, 3 Pages.
International Search Report issued in PCT/US2004/027836 dated Dec. 30, 2004, 1 Page.
Japanese office action dated Jul. 9, 2010 for JP 2007-505113. (in Japanese with English translation).
Supplementary European Search Report dated Nov. 20, 2013 from corresponding EP Application No. 05733012.8.
Trireme Medical, LLC. v. Angioscore, Inc., Complaint for Correction of Inventorship filed in the United States District Court, Northern District of California on Jun. 25, 2014, Case No. 14-cv-02946-LB.
Trireme Medical, LLC. v. Angioscore, Inc., Answer to Complaint filed in the United States District Court, Northern District of California on Aug. 18, 2014, Case No. 14-cv-02946-LB.
Trireme Medical, LLC. v. Angioscore, Inc., Defendant Angioscore's Notice of Motion and Motion to Dismiss filed in the United States District Court, Northern District of California on Jan. 29, 2015, Case No. 14-cv-02946-LB.
Trireme Medical, LLC. v. Angioscore, Inc., Opposition to Defendant Angioscore's Motion to Dismiss filed in the United States District Court, Northern District of California on Feb. 12, 2015, Case No. 14-cv-02946-LB.
Trireme Medical, LLC. v. Angioscore, Inc., Reply in Support of Angioscore's Motion to Dismiss filed in the United States District Court, Northern District of California on Feb. 19, 2015, Case No. 14-cv-02946-LB.
Trireme Medical, LLC. v. Angioscore, Inc., Order Granting Motion to Dismiss entered in the United States District Court, Northern District of California on Mar. 17, 2015, Case No. 14-cv-02946-LB.
Trireme Medical, LLC. v. Angioscore, Inc., Judgement entered in the United States District Court, Northern District of California on Mar. 31, 2015, Case No. 14-cv-02946-LB.
Trireme Medical, LLC. v. Angioscore, Inc., Notice of Appeal filed in the United States District Court, Northern District of California on Mar. 20, 2015, Case No. 14-cv-02946-LB.
Trireme Medical, LLC. v. Angioscore, Inc., Notice of Docketing entered in the United States District Court, Northern District of California on Apr. 1, 2015, Case No. 14-cv-02946-LB.
AngioScore, Inc. v. Trireme Medical LLC et al, Fourth Amended Complaint for: 1) Patent Infringement; 2) Breach of Fiduciary Duty Under California Law; 3) Breach of Fiduciary Duty Under Delaware Law; 4) Aiding and Abetting a Breach of Fiduciary Duty; and 5) Unfair Competition Under California Business and Professional Coss 17200, filed in the United States District Court, Northern District of California, Oakland Division, on Jul. 15, 2014, Case No. 4:12-cv-3393-YGR.
Exhibit A to AngioScore, Inc. v. Trireme Medical, LLC, Fourth Amended Complaint filed Jul. 15, 2014, United States District Court, Northern District of California, Oakland Division, Case No. 4:12-cv-3393-YGR.
AngioScore, Inc. v. Trireme Medical, LLC, Order Construing Claims in Dispute; Granting in Part and Denying in Part Defendants' Motion for Summary Judgment of Non-Infrignment, filed Jun. 25, 2014, United States District Court, Northern District of California, Oakland Division, Case No. 4:12-cv-3393-YGR.
AngioScore, Inc. v. Trireme Medical, LLC, Partial Portion of Reporter's Transcript of Proceedings, Sep. 21, 2015, vol. 12, United States District Court, Northern District of California, Oakland Division, Case No. 4:12-cv-3393-YGR (including testimony by Robert Farnan).
AngioScore, Inc. v. Trireme Medical, LLC, Partial Portion of Reporter's Transcript of Proceedings, Sep. 22, 2015, vol. 13, United States District Court, Northern District of California, Oakland Division, Case No. 4:12-cv-3393-YGR (including testimony by Ali Almedhychy).
AngioScore, Inc. v. Trireme Medical, LLC, Partial Portion of Reporter's Transcript of Proceedings, vol. 14, Sep. 28, 2015, United States District Court, Northern District of California, Oakland Division, Case No. 4:12-cv-3393-YGR [including testimony by Michael Horzewski, jury instructions including meaning of claim terms, and closing arguments).
AngioScore, Inc. v. Trireme Medical, LLC, Defendant's Exhibit DX4222, United States District Court, Northern District of California, Oakland Division, Case No. 4:12-cv-3393-YGR (U.S. Pat. No. 5,797,935 to Barath).
AngioScore, Inc. v. Trireme Medical, LLC, Defendant's Exhibit DX4224, United States District Court, Northern District of California, Oakland Division, Case No. 4:12-cv-3393-YGR (U.S. Pat. No. 5,868,783 to Tower).
AngioScore, Inc. v. Trireme Medical, LLC, Defendant's Exhibit DX4268, United States District Court, Northern District of California, Oakland Division, Case No. 4:12-cv-3393-YGR (U.S. Pat. No. 5,730,698 to Fischell et al.).
AngioScore, Inc. v. Trireme Medical, LLC, Defendant's Exhibit DX4272, United States District Court, Northern District of California, Oakland Division, Case No. 4:12-cv-3393-YGR (U.S. Pat. No. 6,059,811 to Pinchasik et al.).
AngioScore, Inc. v. Trireme Medical, LLC, Defendant's Exhibit DX4273, United States District Court, Northern District of California, Oakland Division, Case No. 4:12-cv-3393-YGR (U.S. Pat. No. 6,261,319 to Kveen et al.).
AngioScore, Inc. v. Trireme Medical, LLC, Defendant's Exhibit DX4274, United States District Court, Northern District of California, Oakland Division, Case No. 4:12-cv-3393-YGR (U.S. Pat. No. 6,416,539 to Hassdenteufel).
AngioScore, Inc. v. Trireme Medical, LLC, Defendant's Exhibit DX4315, United States District Court, Northern District of California, Oakland Division, Case No. 4:12-cv-3393-YGR (Zarge, et al., Chapter 17: Balloon Angioplasty, in Peripheral Endovascualr Insterventions (1996)).
AngioScore, Inc. v. Trireme Medical, LLC, Defendants Exhibit DX4362, United States District Court, Northern District of California, Oakland Division, Case No. 4:12-cv-3393-YGR, (Palmaz, et al., "Atherosclerotic Rabbit Aortas: Expandable Intraluminal Grafting," Radiology, Sep. 1986, pp. 724-726).
AngioScore, Inc. v. Trireme Medical, LLC, Defendants Exhibit DX4473, United States District Court, Northern District of California, Oakland Division, Case No. 4:12-cv-3393-YGR (U.S. Pat. No. 5,196,024 to Barath).
AngioScore, Inc. v. Trireme Medical, LLC, Verdict Form ftiled Sep. 29, 2015, United States District Court, Northern District of California, Oakland Division, Case No. 4:12-cv-3393-YGR.
AngioScore, Inc. v. Trireme Medical, LLC, Judgement as Modified by the Court, filed Oct. 14, 2015, United States District Court, Northern District of California, Oakland Division, Case No. 4:12-cv-3393-YGR.
Trireme Medical, LLC v. AngioScore, Inc., Decision on Appeal dated Feb. 5, 2016, United States Court of Appeals for the Federal Circuit, Case No. 2015-1504.

* cited by examiner

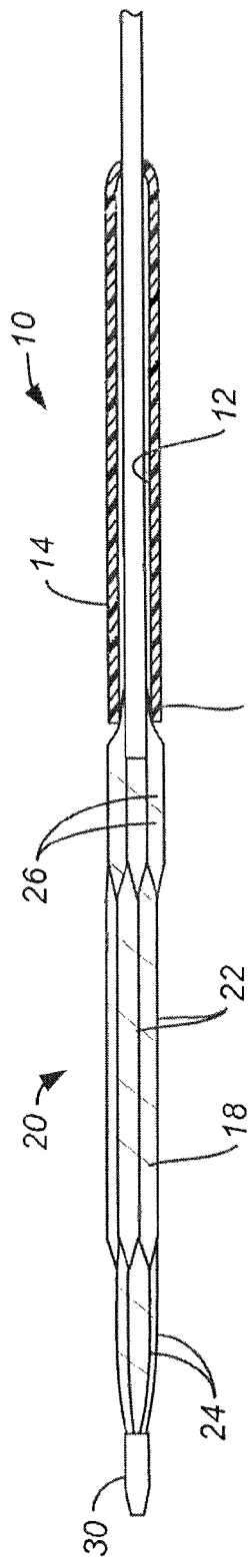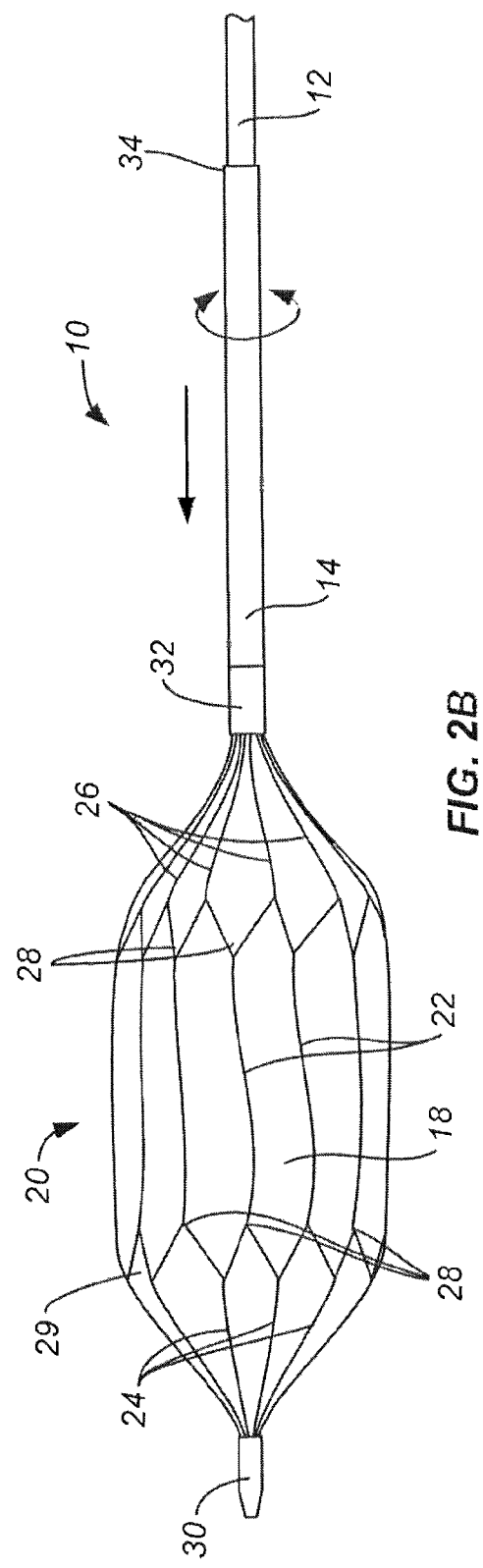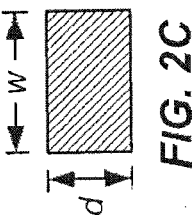

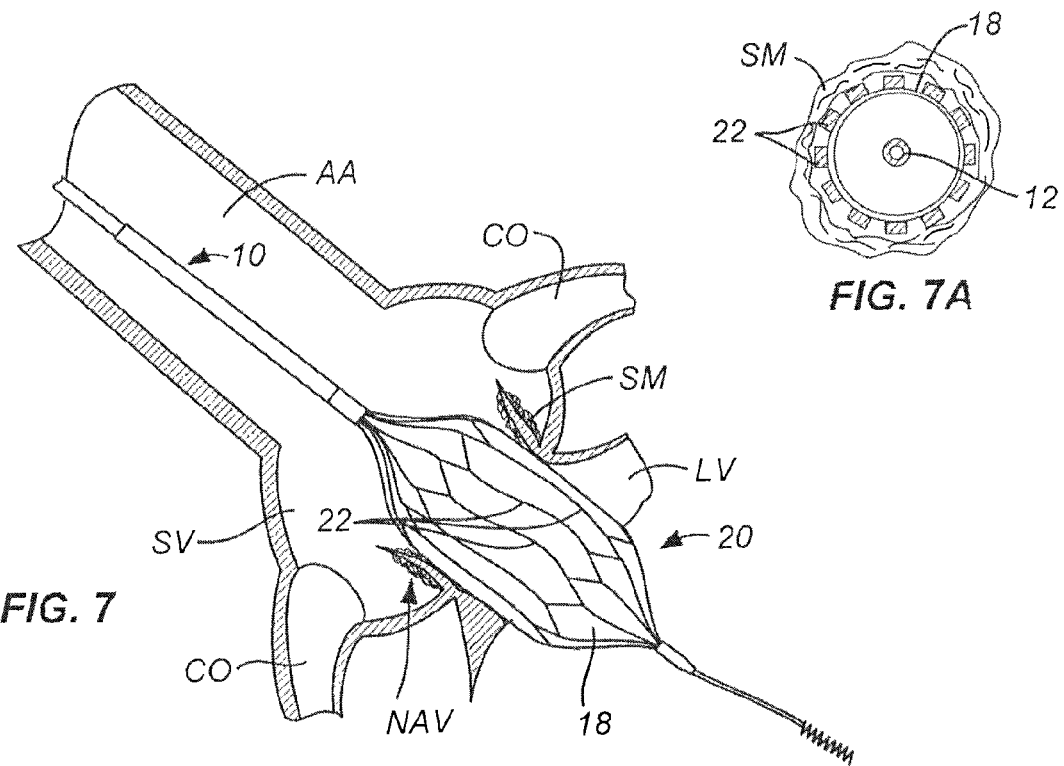
*FIG. 7*
*FIG. 7A*
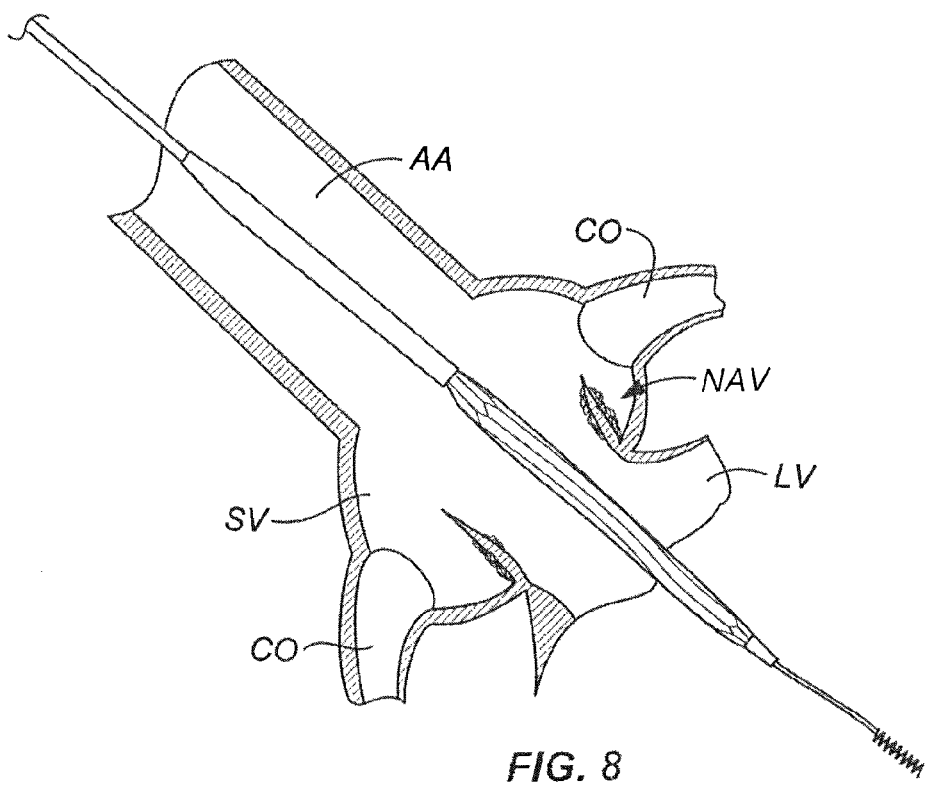
*FIG. 8*

METHOD AND SYSTEM FOR TREATING VALVE STENOSIS

CROSS REFERENCE TO RELATED APPLICATIONS

This application is a divisional of co-pending U.S. patent application Ser. No. 13/236,449 filed on Sep. 19, 2011, which claims the benefit under 35 U.S.C. 119 of U.S. Provisional Patent Application No. 61/384,800, filed Sep. 21, 2010, the full disclosures of which are incorporated herein by reference.

BACKGROUND OF THE INVENTION

1. Field of the Invention

The present invention relates generally to medical devices and methods. More particularly, the present invention relates to the use of an expandable scoring cage for disrupting stenotic deposits in cardiac valves.

Stenosis of the aortic and other cardiac valves occurs when the valve annulus narrows restricting the flow of blood through the valve when open. This is a particular problem with aortic valve stenosis where the flow of oxygenated blood from the left ventricle to the rest of the body is limited. When the aortic valve is obstructed, the heart must pump at a higher pressure to overcome the increased resistance which can weaken the heart and lead to various symptoms, such as fatigue, chest pain, heart palpitation, heart murmur, and ultimately heart failure. The traditional treatment for aortic valve stenosis has been heart valve replacement through open chest, stopped heart procedures. Recently, percutaneous heart valve replacement has become available. For many patients, however, heart valve replacement is not a realistic choice. Some patients are too weak or ill to undergo such procedures. Other patients are at the beginning stages of valve stenosis where performing a valve replacement procedure might not be justified.

For such patients, it would be desirable to provide alternative therapeutic procedures. Valve angioplasty is one such alternative procedure. A balloon catheter is introduced to the aortic valve, typically through an aortic arch approach, and the balloon inflated within the heart valve to disrupt and loosen stenotic material located on the valve leaflets and in the valve annulus. While such procedures have been clinically employed, they suffer from a number of shortcomings. The principal shortcoming is a lack of effectiveness in some patients. The radial pressure applied by the balloons is not always directed symmetrically, and the balloons can often slip from their original placement within the valve annulus. Both these circumstances limit the effectiveness of conventional valvuloplasty therapy. Moreover, the valvuloplasty balloons must be very large (in order to accommodate the valve annulus), thus requiring a relatively long deflation period. Since the aorta can only be blocked for a short period of time, the need to provide for a lengthy deflation time limits the treatment time in which the balloon can be fully inflated. Additionally, the deflation of such large balloons often leaves a very uneven profile with flaps and portions of the balloon extending radially outwardly. The removal of such structures from the valve annulus can damage the fragile valve leaflets as well as the vasculature through which the catheter is removed. Additionally, valvuloplasty has generally been limited to the treatment of aortic valves.

For these reasons, it would be desirable to provide improved apparatus and methods for performing cardiac valve angioplasty. It would be particularly useful if the methods and apparatus provided for more effective treatment of cardiac valve stenoses, not only in the aorta but in other cardiac valves as well, such as the mitral valve and the pulmonary valve. It would be further desirable to provide valvuloplasty balloons which are capable of applying force symmetrically about their perimeter in order to more effectively treat and fracture stenotic material surrounding the valve annulus. It would be still further desirable if the valvuloplasty balloons were able to resist slippage while inflated, thus improving effectiveness and reducing the risk of left ventricular perforations. It would be still further useful if the valvuloplasty balloons were adapted for rapid deflation so that the period of inflation intended to treat the valve could be prolonged. Additionally, it would be useful if the valvuloplasty balloons folded in a regular manner with a low profile to facilitate removal of the balloons and reduce the risk of trauma to the valve leaflets or other harder vascular structures. At least some of these objectives will be met by the invention as described herein below.

2. Description of the Background Art

Catheters for treating cardiac valve stenoses are described in the following U.S. Patents and Published Applications: U.S. Pat. Nos. 4,986,830; 5,443,446; 6,746,463; 7,029,483; 7,455,652; US 2005/0137690; and 2006/0074484. Commonly owned patents and pending applications which relate to the invention herein include: U.S. Pat. Nos. 7,686,824; 7,691;119; 2004/0243158; 2005/0021071; 2005/0021070; 2006/0259005; 2006/0085025; 2009/0105687; and 2010/0121372, the full disclosures of which are incorporated herein by reference.

BRIEF SUMMARY OF THE INVENTION

The present invention provides improved apparatus and methods for performing valvuloplasty of the aortic and other cardiac valves, such as the pulmonary valve and the mitral valve. Valvuloplasty is the treatment of stenotic cardiac valves by balloon expansion within the valve annulus. Such balloon expansion can open the valve and increase the area available for blood flow by fracturing and displacing stenotic material, such as calcified plaque, which covers the valve leaflets and/or the valve annulus. Such stenotic valves become stiff such that functioning of the valve leaflets deteriorates, including a reduced opening of the leaflets available to allow blood flow during ventricular systole.

The present invention provides for placement of scoring elements over the exterior surface of a balloon or other expansible shell. The scoring elements, which typically number from six to twenty, are preferably uniformly distributed over the outer surface of the balloon so that they concentrate forces uniformly over the circumference of the valve annulus when the balloon is inflated. Such uniformly concentrated forces are able to effectively fracture and displace the stenotic material to increase the area of the annulus available for blood flow and often to improve the ability of the valve leaflets to function. Additionally, when the scoring elements are incorporated in a self-closing elastic cage which is placed over the balloon, the cage is able to improve balloon deflation characteristics so that the balloon deflates both more rapidly and more uniformly so that balloon flaps and other elements are not exposed during withdrawal of the balloon from the valve annulus and vasculature. The scoring elements also help to stabilize the balloon within the valve annulus during balloon inflation to inhibit slippage which can both reduce the effectiveness of the treatment and expose the valve annulus and surrounding tissue to damage.

In a first aspect of the present invention, a method for treating for cardiac valve stenoses comprising positioning an expansible shell inside a stenosed cardiac valve annulus. The shell is expanded to engage a plurality of scoring elements present on an external surface of the shell against the annulus. The shell expansion is maintained for a time sufficient for the scoring elements to disrupt the stenoses, after which time the shell is contracted and removed from the valve annulus together with the scoring elements.

Positioning the expansible shell typically comprises advancing a catheter which carries the expansible shell and scoring elements over the aortic arch and into the aortic valve annulus. The shell expansion will typically be maintained in a period of time from 1 second to 10 seconds, usually from 1 second to 4 seconds, typically for about 2 seconds. When using an inflatable balloon, expanding the shell comprising expanding the balloon, and the scoring elements are typically provided as axial struts in an elastic metal cage surrounding but unattached to the inflatable balloon. The cage is elastically biased to close over the balloon as the balloon is inflated, thus both decreasing the deflation time and improving the rewrap characteristics of the balloon over the placement catheter. In the exemplary embodiments, the balloon is non-distensible and inflated to a pressure in the range from 1 atmosphere to 12 atmospheres, preferably from 4 atmospheres to 12 atmospheres, typically about 8 atmospheres. The balloon will usually carry from six to twenty scoring elements and will be inflated to a diameter in the range from twenty millimeters to thirty millimeters, depending on the size of the valve annulus being treated.

In a second aspect, the present invention provides devices for treating cardiac valve stenoses. The devices comprise a shaft having a proximal end and a distal end and an expansible shell carried on a distal region of the shaft. A plurality of scoring elements are carried by the expansible shell, typically over its exterior surface. The expansible shell typically has a length and expanded diameter selected to fully occupy an adult human cardiac valve annulus, typically the aortic valve annulus, and said scoring elements have flat radially outward surfaces for engaging the stenotic material when inflated within a stenosed cardiac valve.

The shaft may be adapted to be introduced over the aortic arch to position the expansible shell in the aortic or other cardiac valve annulus. The expansible shell is preferably a non-distensible inflatable balloon having an inflated diameter (when fully inflated) in the range from twenty millimeters to thirty millimeters. The length of the inflatable balloon will be relatively short, typically in the range from two centimeters to four centimeters. Such a short length may be used because the balloon with the scoring elements thereon is much less likely to be axially displaced when inflated than is a bare balloon. The balloon will typically carry from six to twenty scoring elements, preferably from eight to sixteen scoring elements, which scoring elements extend from a proximal end to a distal end of the balloon and are evenly circumferentially spaced-apart over an exterior surface of the balloon.

The scoring elements are typically formed as axial struts in an elastic metal cage structure. The cage structure is coupled to the catheter shaft but not attached to the expansible balloon. The cage is elastically biased to close to a diameter in the range from three millimeters to seven millimeters when the shell is unexpanded.

In an exemplary embodiment, the elastic metal cage structure comprises a plurality of circumferentially arranged, axially elongated hexagonal cells, where each cell has a proximal connection point and a distal connection at longitudinally opposed ends of the cell. Axial struts are connected to each of the connection points, and the struts are used to connect the cage structure to the catheter shaft. At the distal end, the axial struts are connected directly to the catheter shaft. In contrast, at the proximal end, the axial struts are connected to a compliance tube, where the compliance tube is disposed coaxially over the catheter shaft and attached to the catheter shaft only at a proximal end of the compliance tube. The axial connector links at the proximal end of the elastic metal cage structure are attached to a distal end of the compliance tube. In this way, the compliance tube can accommodate both axial foreshortening of the cage as the balloon is radially expanded as well as to accommodate any rotational, torsional forces experienced by the cage structure as the balloon is expanded.

The scoring elements have dimensions particularly selected to score stenotic material present on cardiac valves. Typically, the scoring elements have rectangular cross-sections with a height (thickness) in the radial direction in the range from 0.1 millimeters to 0.4 millimeters, usually 0.15 millimeters to 0.25 millimeters, and a width in the circumferential direction in the range from 0.25 millimeters to 0.5 millimeters, preferably from 0.3 millimeters to 0.4 20 millimeters.

BRIEF DESCRIPTION OF THE DRAWINGS

FIGS. 2A and 2B illustrate an expansible shell of the valvuloplasty catheter of FIG. 1 carrying a self-closing elastic cage comprising a plurality of scoring elements, where the balloon and cage are in their contracted configuration in FIG. 2A and in their expanded configuration in FIG. 2B.

FIG. 2C is a cross-sectional view of an individual scoring element of the cage of FIGS. 1, 30 2A, and 2B.

FIGS. 5-8 and 7A illustrate use of the valvuloplasty catheter of FIG. 1 in treating an aortic valve in accordance with the principals of the present invention.

DETAILED DESCRIPTION OF THE INVENTION

Figure 1:
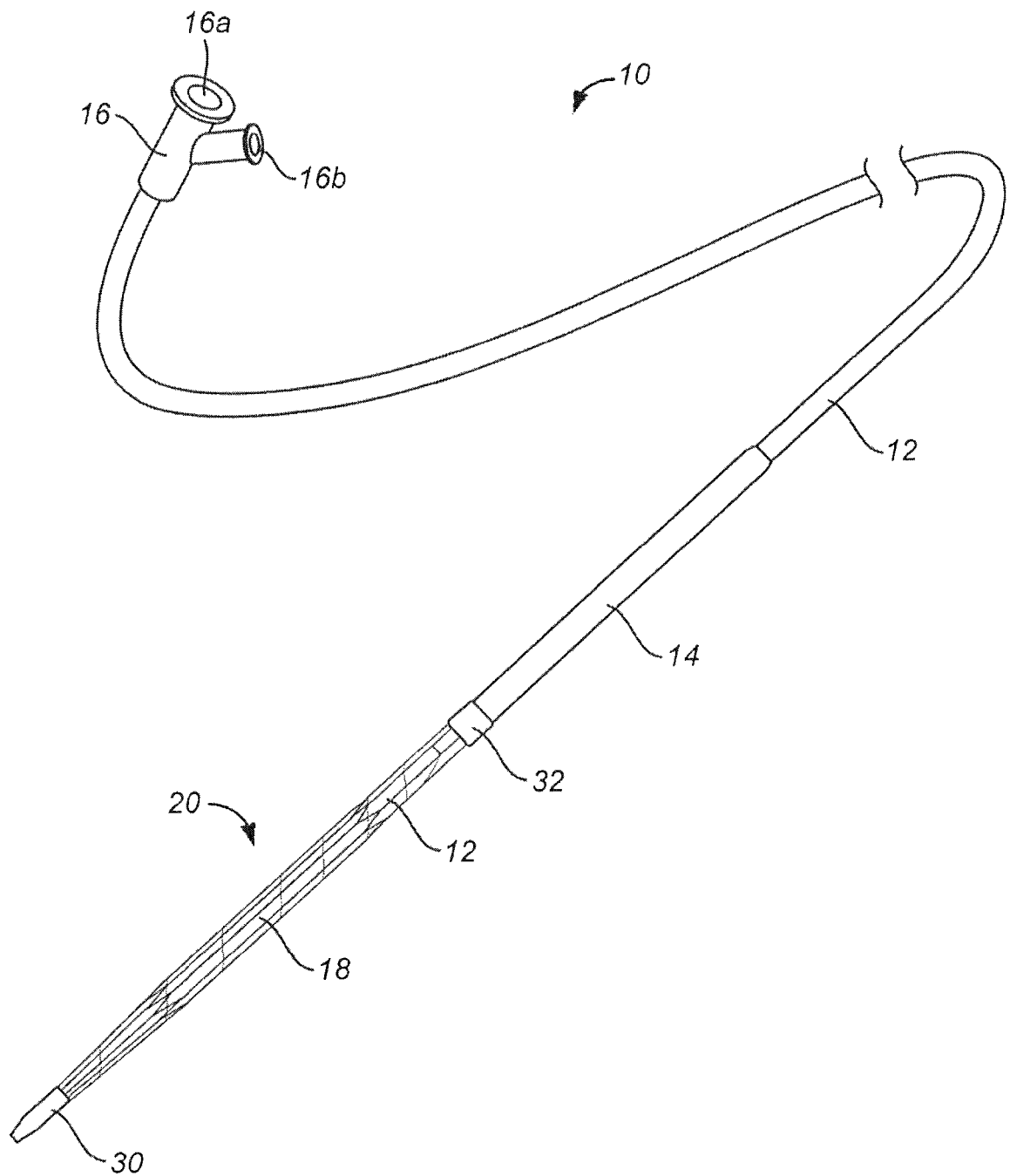
FIG. 1 is a prospective view of a valvuloplasty catheter constructed in accordance with the principals of the present invention.

A valvuloplasty catheter 10 constructed in accordance with the principals of the present invention is illustrated in FIGS. 1, 2A, and 2B. The valvuloplasty catheter 10 comprises a shaft 12 having a compliance tube 14 coaxially disposed over a distal portion thereof. A proximal hub 16 includes an axial guide wire port 16a and a side balloon inflation port 16b. The guide wire port 16a attaches to a guide wire lumen which extends axially over the entire length of catheter shaft 12. The balloon inflation port 16b connects to an inflation lumen, typically formed in a wall of the shaft 12.

An expansible shell 18 is located at the distal end of the catheter shaft 12 and connected to receive inflation medium from the inflation lumen in the shaft which is connected to port 16b. In this way, the balloon can be inflated from a contracted or non-inflated configuration, as shown in FIG. 2A, to a fully inflated configuration, as shown in FIG. 2B.

An expansible metal cage 20 is mounted over the expansible shell (typically an inflatable balloon) 18 so that it expands with the inflated shell or balloon 18, as shown in FIG. 2B, and self-closes over the balloon, as shown in the contracted configuration of FIG. 2A. The elastic metal cage is typically formed from a highly elastic metal, such as nitinol or spring stainless steel, and may typically be formed by laser cutting of a nitinol or stainless steel hypo tube.

In a preferred configuration, the elastic metal cage will comprise hexagonal cells which extend over the middle of the expansible shell when inflated, as best seen in FIG. 2B. The hexagonal cells comprise parallel (axially aligned) scoring elements 22 which are the components which engage and score the stenotic material in the valve annulus when the shell 18 is expanded, as will be described in more detail with FIGS. 6-8 below. In order to maintain an equal circumferential spacing of the scoring elements 22, each end of the scoring element is connected at a connection point 28 to points on a zig zag ring 29 which are in turn connected to distal connecting links 24 at the distal end of the cage and proximal connecting links 26 at the proximal end of the cage. The distal connecting links 24, in turn, are attached to the catheter shaft 12 by a distal collar 30, while the proximal connector links 26 are connected to the compliance tube 14 by a proximal collar 32. The compliance tube 14 is unattached to the catheter shaft 12 except for an attachment point 34 at its proximal end. In this way, when the expansible shell 18 is inflated or otherwise radially expanded, the compliance tube 14 can elongate (in the direction of the linear arrow in FIG. 2B) to accommodate any foreshortening and can also torque or rotate, as shown by the circular arrow in FIG. 2B.

Figure 3:
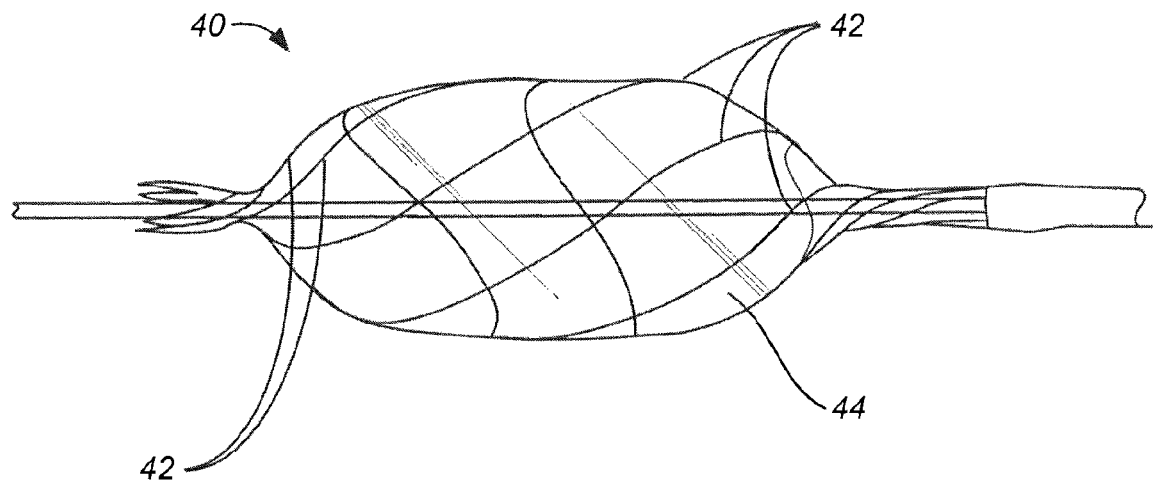
FIGS. 3 and 4 illustrate alternative self-closing cage configurations in accordance with the principals of the present invention.
Figure 4:
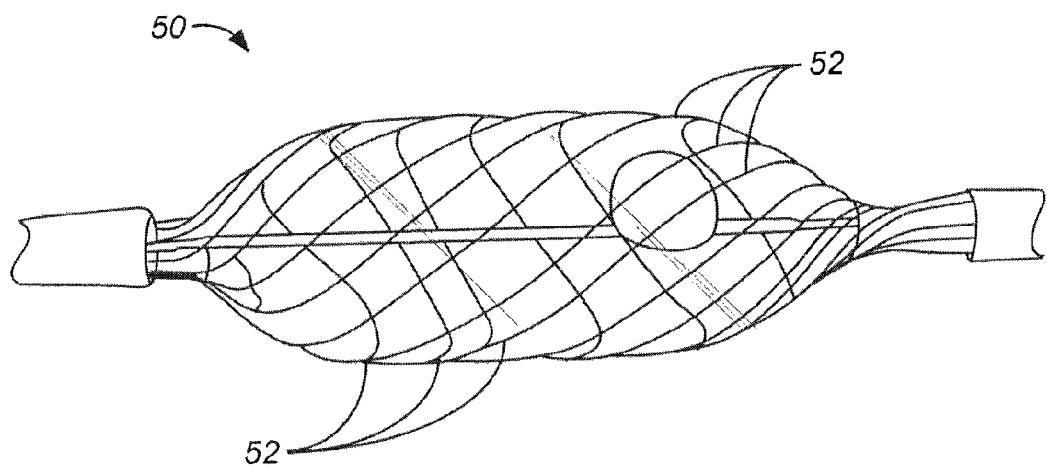

Although the illustrated structure of elastic metal cage 20 is presently preferred as it effectively maintains equal circumferential spacing of the scoring elements 22 as the shell 18 is inflated or otherwise expanded, other shell designs could be employed, such as those having helical scoring elements, as illustrated in FIGS. 3 and 4. In FIG. 3, a cage 40 comprising six helical scoring elements 42 disposed over an inflatable balloon 44. The construction of the catheter which carries balloon 44 and cage 40 will generally be the same as that described with respect to the catheter of FIG. 1. FIG. 4 also describes an expansible cage 50 having a plurality of helical scoring elements 52 where the principal difference is that cage 50 includes twelve scoring elements in contrast to the six scoring elements of cage 40 of FIG. 3.

Figure 5:
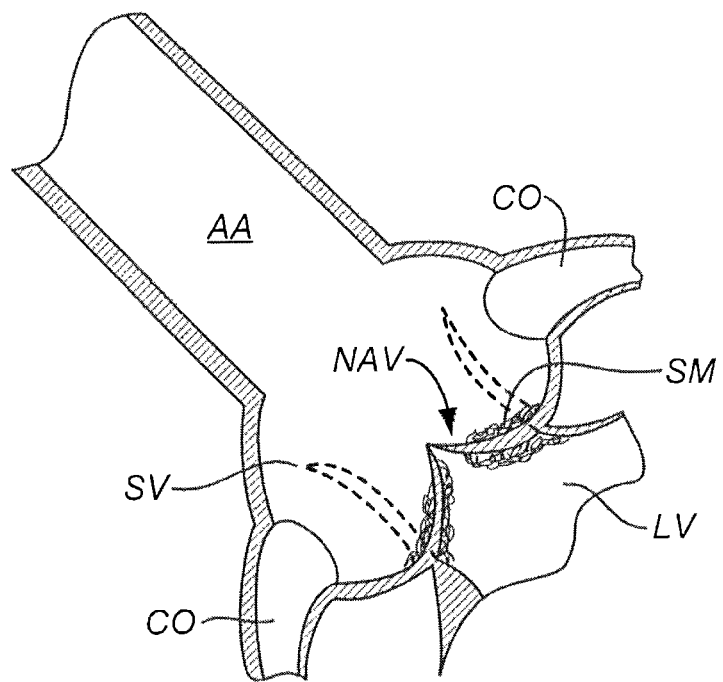

Referring now to FIGS. 5-8, use of the valvuloplasty catheter 10 of FIG. 1 in treating a stenosed aortic valve will be described. The stenosed aortic valve NAV is illustrated in FIG. 5, where the stenotic material SM is present on both the valve leaflets and the valve annulus. While the valve can function, the ability of the valve leaflets to fully open and close is hindered, limiting the blood flow through the open valve and/or allowing leakage through the closed valve. The aortic valve NAV is at the base of the aortic arch AA and adjacent to the Sinus of Valsalva SV. The coronary arteries open off the coronary ostia CO, and the valve NAV opens to permit blood flow from the left ventricle LV into the aortic arch.

Figure 6:
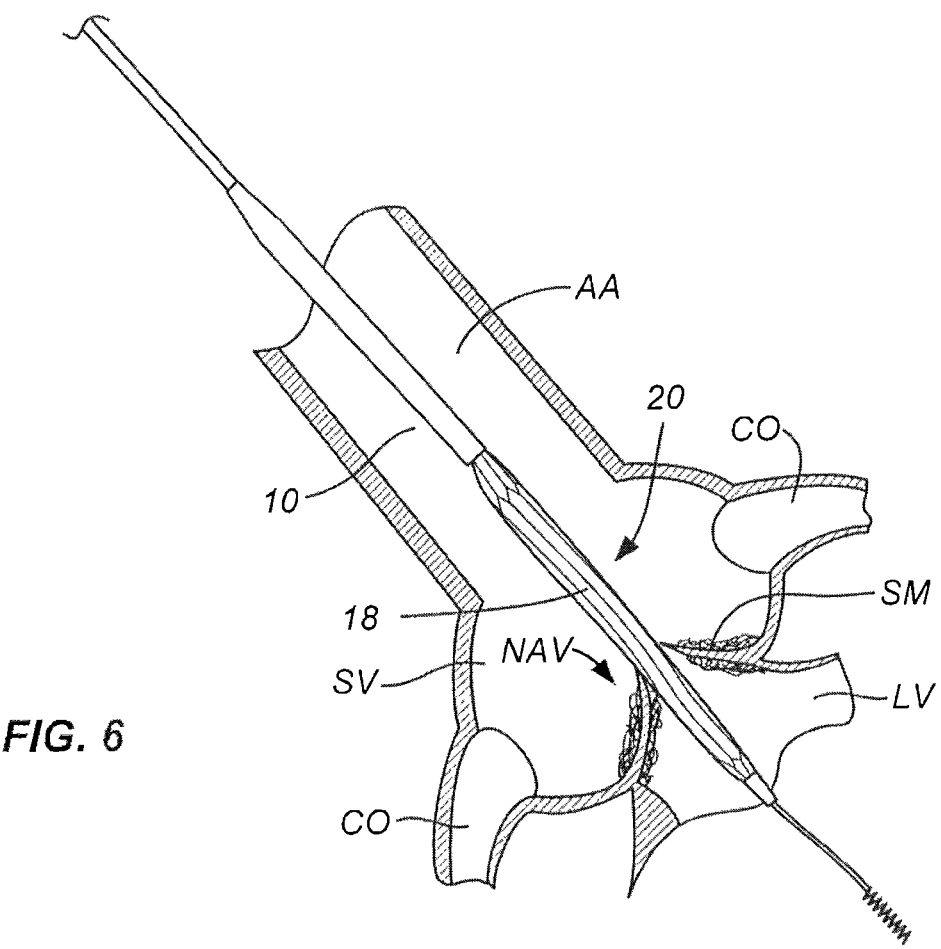

Referring now to FIG. 6, the valvuloplasty catheter 10 is introduced so that the elastic metal cage 20 carried on the expansible shell/balloon 18 is introduced through the valve leaflets into the annulus of the aortic valve NAV. After the catheter 10 is properly positioned, as shown in FIG. 7, the expansible shell 18 is inflated to engage the individual scoring elements 22 against the stenotic material SM around the valve annulus, as shown in FIG. 7A. Note that the cross-sections of the scoring elements 22 are not shown to scale and are actually smaller relative to the expansible shell 18 than illustrated.

After inflating the balloon for a desired period of time, typically from 1 second to 10 seconds, usually from 1 second to 4 seconds, the balloon is rapidly deflated so that the elastic metal cage closes over the balloon, rewrapping the balloon in a compact package, as shown in FIG. 8. Catheter 10 may then be withdrawn and the treatment is completed.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating cardiac valve stenoses, said method comprising:
   providing a device, comprising:
      a shaft having proximal and distal ends;
      an expansible shell carried on a distal region of the shaft;
      a plurality of nondeployable scoring elements carried by the shaft;
      wherein the expansible shell has a length and expanded diameter selected to fully occupy an adult human cardiac valve annulus and the scoring elements have flat radially outward surfaces;
      wherein the shaft is a catheter shaft adapted to be introduced over the aortic arch to position the expansible shell in the cardiac valve annulus;
      wherein the expansible shell is a nondistensible inflatable balloon;
      wherein the scoring elements extend from a proximal end to a distal end of the balloon and are circumferentially spaced over an exterior balloon surface;
      wherein the scoring elements are struts in an elastic metal cage structure and parallel to its axis, wherein the cage structure is carried by the catheter shaft, wherein the cage is elastically biased to contract when the balloon is not inflated;
      wherein the elastic metal cage structure comprises circumferentially arranged elongated hexagonal cells which are parallel to the axis, wherein each cell has a proximal connection point to a proximal ring and a distal connection point to a distal ring and where the struts extend between the connection points;
      wherein the cage further comprises distal connector links which extend between the distal connection point and the catheter shaft, the distal links being fixed relative to the distal end of the shaft; and
      further comprising a compliance tube having a distal end coupled to proximal connector links of the cage, the distal end of the compliance tube being movable relative to the shaft, and the compliance tube further having a proximal end fixed to the catheter shaft, wherein the compliance tube is adapted to accommodate axial elongation and circumferential rotation of the cage structure;
   positioning the balloon inside a stenosed cardiac valve annulus;
   expanding the balloon to engage the scoring elements against the annulus;
   maintaining the balloon expansion for a time sufficient for the scoring elements to disrupt the stenoses; and
   contracting the balloon.

2. A method as in claim 1, wherein positioning comprises advancing the shaft over the aortic arch into the aortic valve annulus.

3. A method as in claim 1, wherein the balloon expansion is maintained for a time in the range from 1 second to 12 seconds.

4. A method as in claim 3, wherein expanding the balloon comprises inflating the balloon.

5. A method as in claim 4, wherein the balloon is inflated to a pressure in the range from 1 atm to 12 atm.

6. A method as in claim 5, wherein the balloon is inflated to a diameter in the range from 20 mm to 30 mm.

* * * * *